US00PP25155P3

(12) United States Plant Patent
Danziger

(10) Patent No.: US PP25,155 P3
(45) Date of Patent: Dec. 9, 2014

(54) ***LOBULARIA* PLANT NAMED 'DLOBU21'**

(50) Latin Name: *Lobularia maritima*
Varietal Denomination: DLOBU21

(71) Applicant: Gavriel Danziger, Moshav Mishmar Hashiva (IL)

(72) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 0 days.

(21) Appl. No.: 13/986,065

(22) Filed: Mar. 27, 2013

(65) Prior Publication Data

US 2014/0298550 P1 Oct. 2, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP21,594 P2 * 12/2010 Wicki ..... Plt./263.1

* cited by examiner

*Primary Examiner* — June Hwu
*Assistant Examiner* — Keith Robinson
(74) *Attorney, Agent, or Firm* — Cassandra Bright

(57) ABSTRACT

A new and distinct *Lobularia* cultivar named 'DLOBU21' is disclosed, characterized by large, long lasting flowers. The new variety possesses a moderate semi-trailing habit and is freely branching and strongly structured. The new variety is a *Lobularia*, normally produced as an outdoor garden or container plant.

2 Drawing Sheets

Figure 1:
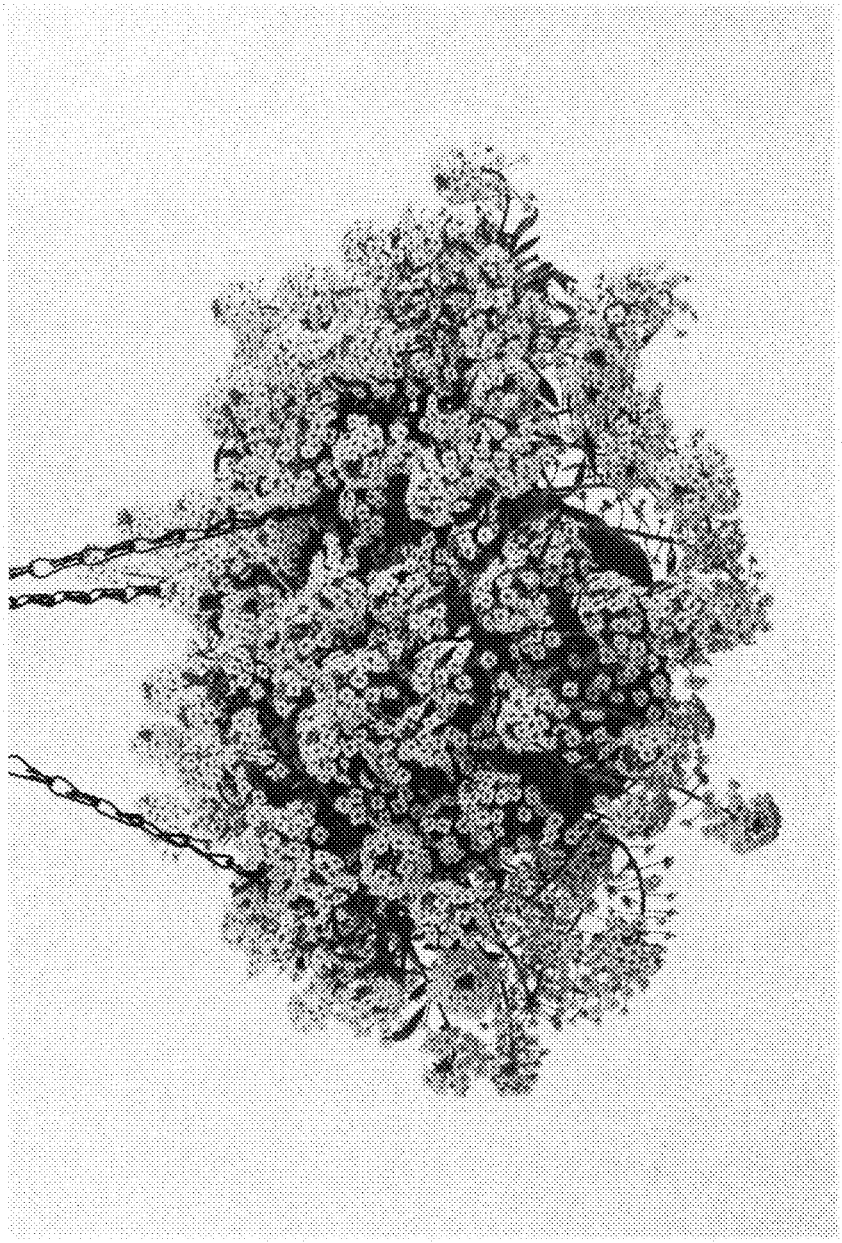

Latin name of the genus and species: *Lobularia maritima*.
Variety denomination: 'DLOBU21'.

BACKGROUND OF THE INVENTION

The new *Lobularia* cultivar is a product of a planned breeding program conducted by the inventor, Gavriel Danziger, in Moshav Mishmar Hashiva, Israel. The objective of the breeding program was to produce new *Lobularia* varieties for ornamental commercial applications. The open pollination resulting in this new variety was made during October of 2010.

The seed parent is the unpatented, proprietary seedling variety referred to as *Lobularia maritima* 'AY-10-106' The pollen parent is unknown as it was an open pollination breeding program. The new variety was discovered in March of 2011 by the inventor in a group of seedlings resulting from the 2010 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during March of 2011 and has shown that the unique features of this cultivar are stable and reproduced true to type in successive generations.

SUMMARY OF THE INVENTION

The cultivar 'DLOBU21' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBU21' These characteristics in combination distinguish 'DLOBU21' as a new and distinct *Lobularia* cultivar:

1. Semi-trailing habit.
2. Long flowering period.
3. Freely branching and strong plant structure.
4. Large flower size.
5. Moderate vigor.

Plants of the new cultivar 'DLOBU21' are similar to plants of the seed parent, *Lobularia maritima* 'AY-10-106' in most horticultural characteristics, however, plants of the new cultivar 'DLOBU21' are faster growing than plants of the seed parent 'AY-10-106'. 'DLOBU21' is more floriferous than seed parent 'AY-10-106'. Additionally 'DLOBU21' produces a bushier more compact, less trailing plant habit than seed parent 'AY-10-106'.

COMMERCIAL COMPARISON

Plants of the new cultivar 'DLOBU21' are comparable to the variety *Lobularia* 'Inlbusnopr' U.S. Plant Pat. No. 21,594. The two *Lobularia* varieties are similar in most horticultural characteristics; however, the new variety 'DLOBU21' differs in producing a compact and less vigorous plant than comparator 'Inlbusnopr'. Also 'DLOBU21' produces smaller leaves, as well as a shorter inflorescence than comparator 'Inlbusnopr'. Additionally, plants of 'DLOBU21' are not sterile like those of the comparator 'Inlbusnopr'.

Plants of the new cultivar 'DLOBU21' are comparable to the unpatented commercial variety *Lobularia* 'Snow Crystal'. The two *Lobularia* varieties are similar in most horticultural characteristics, however, the new variety 'DLOBU21' differs in producing darker leaves and larger flowers than those of comparator 'Snow Crystal'. Additionally, 'DLOBU21' flowers over a longer period than the comparator, 'Snow Crystal'.

BRIEF DESCRIPTION OF THE PHOTOGRAPHS

The accompanying photograph in FIG. 1 illustrates in full color a typical plant of 'DLOBU21' grown in a greenhouse, in a 13 cm pot. Age of the plant photographed is approximately 6 weeks from a sticking.

Figure 2:
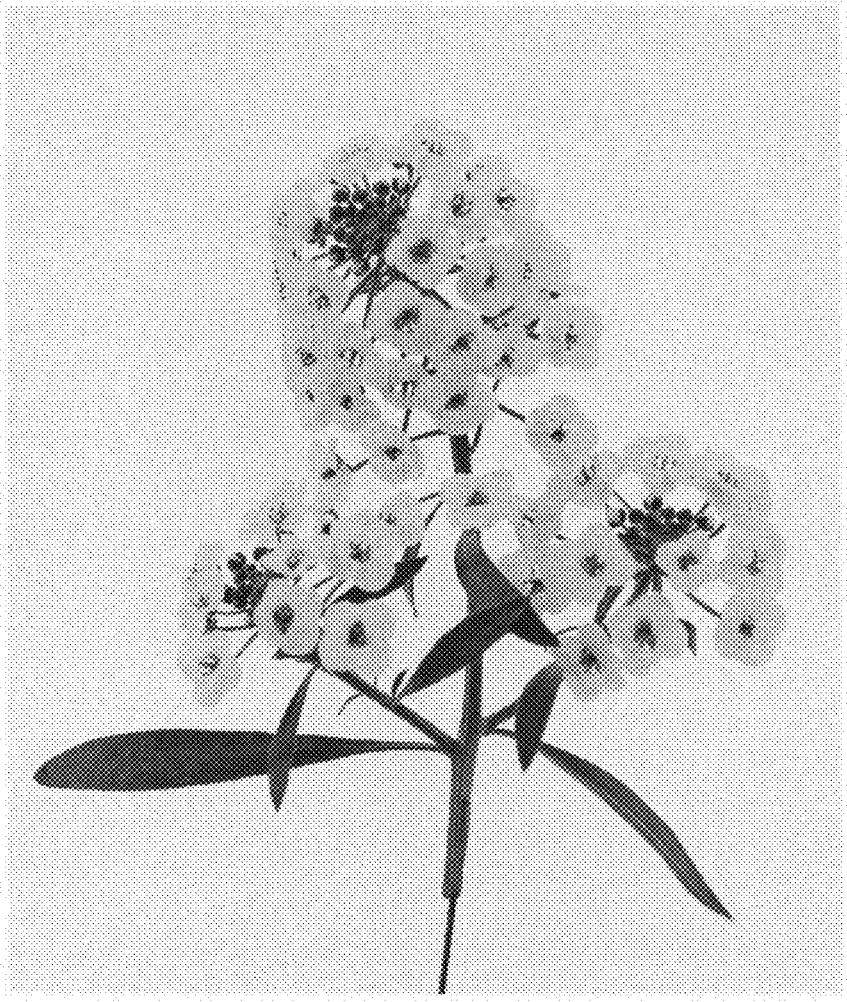

FIG. 2 illustrates in full color a close up of a typical bloom of 'DLOBU21'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DLOBU21' plants grown in a greenhouse during Autumn to Spring in Moshav Mishmar Hashiva, Israel. The growing temperature ranged from 18° C. to 30° C. during the day and from 9° C. to 16° C. during the night. General light conditions are high light levels of 60,000 to 90,000 lux. Measurements and numerical values represent averages of typical plant types.

Botanical classification: *Lobularia maritima* 'DLOBU21'.

PROPAGATION

Typical propagation material: Cuttings.
Time to rooting: 14 to 20 days at approximately 16° C.
Root description: Thin, fibrous, freely branching. Near White group RHS 155C in color.

PLANT

Age of plant described: Approximately 8 weeks.
Growth habit: Compact (Semi trailing and dense).
Height: Approximately 15 cm.
Plant spread: Approximately 30 cm. (radius).
Growth rate: Moderate.
Branching characteristics: Freely Branching.
Approximate quantity of lateral branches: Approximately 10 primary lateral branches and numerous secondary and tertiary lateral branches.
Length of lateral branches: Approximately 26 cm.
Diameter of lateral branches: Approximately 0.35 cm.
Texture of lateral branches: Slightly Pubescent.
Lateral branch shape: Hexagonal in cross section.
Lateral branch strength: Strong (good).
Lateral branch color: Approximately Yellow-green group RHS 144A.
Other stem or plant characteristics: Not relevant.
Internode length: 3 cm (average).
Number of leaves per lateral branch: Average 8.

FOLIAGE

Leaf:
- *Arrangement*.—Alternate
- *Shape of blade*.—Oblanceolate. .
- *Average length*.—Approximately 6 cm. ((Mature foliage—9 cm).
- *Average width*.—Approximately 1 cm. ((Mature foliage—2 cm).
- *Apex*.—Acute.
- *Base*.—Cuneate.
- *Attachment*.—Sessile.
- *Margin*.—Entire.
- *Texture of top surface*.—Slightly Pubescent.
- *Texture of bottom surface*.—Slightly Pubescent.
- *Color*.—Young foliage upper side: Near Green group RHS 137B. Young foliage under side: Near Green group RHS 137C. Mature foliage upper side: Near Green group RHS 137B. Mature foliage under side: Near Green group RHS 137C.
- *Venation*.—Pinnate. Indistinguishable from foliage.

Petiole: Not present.

FLOWER

Bloom period:
- *Natural season*.—Long lasting flowering period. From March through December.
- *In commercial production, flowering begins from a rooted cutting in*.—Approximately 4 weeks.

Inflorescence:
- *Arrangement*.—Panicle.
- *Height*.—Approximately 16 cm.
- *Width*.—Approximately 3 cm.
- *Quantity of flowers per inflorescence*.—Approximately 70.

Bud:
- *Bud shape*.—Globose spherical.
- *Bud length*.—Approximately 2 mm.
- *Bud diameter*.—Approximately 1.5 mm.
- *Bud color*.—Near Green group RHS 143A.
- *Rate of opening*.—Individual flowers: Fully open approximately 3 days from the bud stage.

Individual flower:
- *Type of individual flowers*.—Single flower.
- *Quantity of flowers and buds per plant*.—Approximately 70-80 flowers and buds per inflorescence—more than 2000 flowers per plant.
- *Diameter of entire flower*.—Approximately 0.7 cm.
- *Depth of flower*.—Approximately less than 1 mm.
- *Flower longevity on plant*.—Approximately 5 days.
- *Persistent or self-cleaning*.—Self-cleaning.
- *Fragrance*.—Sweet, honey like.

Petals:
- *Length of petal*.—Approximately 4.5 mm.
- *Width of petal*.—Approximately 4 mm.
- *Apex*.—Rounded.
- *Base*.—Reniform.
- *Shape of petal*.—Oval.
- *Petal margin*.—Entire.
- *Petal arrangement*.—4 petals fused in a single whorl.
- *Petal number*.—4 petals.
- *Petal appearance*.—Matte.
- *Petal texture*.—Smooth, glabrous all surfaces.

Color:
- *Upper surface at first opening*.—Near RHS N999D (mini color chart 2005).
- *Upper surface at maturity*.—Near RHS N999D (mini color chart 2005).

*Upper surface at fading*.—Near White group RHS N155D.
*Under surface at first opening*.—Near White group RHS N155D.
*Under surface at maturity*.—Near White group RHS N155D.
*Under surface at fading*.—Near White group RHS N155D.

Petaloids or other floral structures: Not present.

Sepal:
*Number*.—4.
*Sepal appearance*.—4 sepals.
*Sepal arrangement*.—4 sepals in a single whorl.
*Sepal length*.—Approximately 1 mm.
*Sepal width*.—Approximately 0.7 mm.
*Sepal shape*.—Elliptic.
*Base*.—Truncate.
*Apex shape*.—Acute.
*Margin*.—Entire.
*Color*.—Near Green group RHS 143A all surfaces.

Peduncle:
*Length*.—Approximately 2 cm.
*Diameter*.—Approximately 2 mm.
*Angle*.—Not relevant.
*Strength*.—Strong.
*Color*.—Near Green group RHS 143A.

Pedicel:
*Length*.—Approximately 1 cm.
*Diameter*.—Approximately 0.5 mm.
*Angle*.—Approximately 70-90 degrees.
*Color*.—Near Green group RHS 143A.
*Strength*.—Flexible, moderately strong.

REPRODUCTIVE ORGANS

*Number of pistils per flower*.—1.
*Pistil length*.—Approximately less than 1 mm.
*Stigma shape*.—Rounded to broadly spreading.
*Stigma color*.—Near Yellow-green group RHS 144C.
*Style color*.—Near Yellow-green group RHS 144B.
*Style length*.—Approximately 1 mm.
*Ovary color*.—Near Yellow-green group RHS 144C.
*Stamens quantity*.—6.
*Stamen length*.—1.5 mm.
*Anther shape*.—Elliptic.
*Anther size*.—0.5 mm.
*Anther color*.—Near Yellow-orange group RHS 14B.
*Pollen color*.—Near Yellow-orange group RHS 15A.
*Pollen quantity*.—Uncountable.

OTHER CHARACTERISTICS

Disease and pest resistance: Neither resistance nor susceptibility to the normal diseases and pests of *Lobularia* have been observed.

Drought tolerance and cold tolerance: Plants of the new *Lobularia* have been noted to have good tolerance at temperatures from 1° C. to 38° C. and also in rain and wind conditions.

Fruit/seed production: Color and Shape of Fruits and Seeds: The fruits and Seeds are elliptical and flat. The color of the mature seed is near Grey-brown group RHS N199B.

What is claimed is:

1. A new and distinct cultivar of *Lobularia* plant named 'DLOBU21' as herein illustrated and described.

* * * * *